(12) United States Patent
Cho et al.

(10) Patent No.: US 11,168,426 B2
(45) Date of Patent: Nov. 9, 2021

(54) LAUNDRY TREATING APPARATUS

(71) Applicant: SAMSUNG ELECTRONICS CO., LTD., Suwon-si (KR)

(72) Inventors: Hwang Mook Cho, Suwon-si (KR); Eung Ryeol Seo, Suwon-si (KR); Geon Ung Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 94 days.

(21) Appl. No.: 16/324,363

(22) PCT Filed: Jul. 31, 2017

(86) PCT No.: PCT/KR2017/008226
§ 371 (c)(1),
(2) Date: Feb. 8, 2019

(87) PCT Pub. No.: WO2018/030692
PCT Pub. Date: Feb. 15, 2018

(65) Prior Publication Data
US 2019/0169789 A1 Jun. 6, 2019

(30) Foreign Application Priority Data

Aug. 10, 2016 (KR) .................. 10-2016-0101980

(51) Int. Cl.
| | |
|---|---|
| D06F 87/00 | (2006.01) |
| D06F 35/00 | (2006.01) |
| D06F 69/00 | (2006.01) |
| A61L 2/07 | (2006.01) |
| D06F 58/10 | (2006.01) |
| D06F 58/20 | (2006.01) |

(52) U.S. Cl.
CPC ............... *D06F 35/00* (2013.01); *A61L 2/07* (2013.01); *D06F 58/10* (2013.01); *D06F 58/20* (2013.01); *D06F 69/00* (2013.01); *D06F 87/00* (2013.01)

(58) Field of Classification Search
CPC .......... D06F 87/00; D06F 35/00; D06F 58/10; D06F 58/20; D06F 69/00; A61L 2/07
USPC ......................................................... 68/5 C
See application file for complete search history.

(56) References Cited

U.S. PATENT DOCUMENTS

2012/0160269 A1    6/2012    Pyo et al.

FOREIGN PATENT DOCUMENTS

| CN | 202519475 | 11/2012 |
|---|---|---|
| CN | 104532526 | 4/2015 |
| EP | 1 439 258 | 7/2004 |
| EP | 2 471 996 | 7/2012 |
| JP | 2000-296080 | 10/2000 |

(Continued)

OTHER PUBLICATIONS

KR20110048343A—Machine translation (Year: 2011).*

(Continued)

*Primary Examiner* — Tinsae B Ayalew
(74) *Attorney, Agent, or Firm* — Staas & Halsey, LLP

(57) ABSTRACT

Provided is a laundry treating apparatus including a cabinet, a laundry care device movably provided inside the cabinet, wherein the laundry care device includes a jetting unit configured to jet air to the laundry, and a suction unit into which air jetted by the jetting unit, after passing through the laundry, is suctioned. Inside of the laundry treating apparatus is kept pleasant and laundry care efficiency is enhanced.

13 Claims, 17 Drawing Sheets

(56) References Cited

FOREIGN PATENT DOCUMENTS

| KR | 10-2009-0078964 | 7/2009 |
| KR | 10-2010-0121201 | 11/2010 |
| KR | 10-2011-0048343 | 5/2011 |
| KR | 10-2011-0067754 | 6/2011 |
| KR | 10-2012-0074557 | 7/2012 |

OTHER PUBLICATIONS

KR20110067754A—Machine translation (Year: 2011).*
International Search Report dated Nov. 14, 2017 in corresponding International Application No. PCT/KR2017/008226.
Written Opinion of the International Searching Authority dated Nov. 14, 2017 in corresponding International Application No. PCT/KR2017/008226.
Extended European Search Report dated Apr. 16, 2019 from European Patent Application No. 17839710.5, 6 pages.
Chinese Office Action dated Sep. 1, 2020 in corresponding Chinese Patent Application No. 201780049166.4.
Chinese Office Action dated Mar. 24, 2021 from Chinese Application No. 201780049166.4, 13 pages.

* cited by examiner

LAUNDRY TREATING APPARATUS

CROSS-REFERENCE TO RELATED APPLICATIONS

This application is a National Phase application, under 35 U.S.C. § 371, of international application No. PCT/KR2017/008226 filed Jul. 31, 2017, which claims Convention Priority to Korean patent application No. 10-2016-0101980 filed Aug. 10, 2016, the entire disclosures of which are herein incorporated by reference as a part of this application.

TECHNICAL FIELD

The present disclosure relates to a laundry treating apparatus, and more specifically, to a laundry treating apparatus capable of effectively refreshing laundry.

BACKGROUND ART

In general, a laundry treating apparatus may include a washing machine for washing laundry, a drying machine for drying laundry having been washed, a laundry care machine for deodorizing and smoothing wrinkles of laundry.

The laundry care machine serves to jet air, hot air, or steam toward laundry, such that wrinkles are smoothed or laundry is deodorized.

However, contaminants separated from the laundry care machine may be circulated inside the laundry care machine and then adsorbed to the laundry again, which leads to inefficiency in terms of refreshing the laundry.

DISCLOSURE

Technical Problem

One aspect of the present disclosure provides a laundry treating apparatus including a laundry care device having an improved structure.

Another aspect of the present disclosure provides a laundry treating apparatus capable of performing contamination treatment on the entire range of laundry.

Another aspect of the present disclosure provides a laundry treating apparatus capable of keeping the inside thereof uncontaminated and pleasant.

Technical Solution

A laundry treating apparatus according to an aspect of the present disclosure includes: a cabinet; and a laundry care device movably provided inside the cabinet, wherein the laundry care device includes: an jetting unit configured to jet air to the laundry; and a suction unit into which air jetted by the jetting unit, after passing through the laundry, is suctioned.

The laundry care device may be provided to be movable in a first direction, and the jetting unit and the suction unit each are provided with a longitudinal direction that is a second direction perpendicular to the first direction and are disposed in parallel with each other.

The jetting unit and the suction unit may be integrally formed with each other.

The jetting unit may include: a first jetting unit and a second jetting unit disposed symmetrical to each other, the suction unit may include: a first suction unit into which air jetted from the first jetting unit, after passing through the laundry, is suctioned; and a second suction unit disposed symmetrical to the first suction unit and into which air jetted from the second jetting unit, after passing through the laundry, is suctioned, and the first jetting unit and the first suction unit may be movable relative to the first jetting unit and the second suction unit.

The suction unit may be located at a lower side of the jetting unit, and the jetting unit may include a jetting nozzle configured to jet air toward the laundry while being slanted downward, wherein the suction unit may include a filter part directed to the laundry while being slanted upward such that air jetted from the jetting nozzle, after passing through the laundry, is suctioned.

The suction unit may further include: a suction frame provided at an inside thereof with a suction path that allows air suctioned through the filter part to pass therethrough, and on which the filter part is disposed, wherein the jetting unit may further include: a jetting frame provided at an inside thereof with a jetting path that allows air suctioned into the suction path to pass therethrough, and on which the jetting nozzle is disposed.

The jetting nozzle may include a plurality of jetting holes disposed to be spaced apart from each other along a longitudinal direction of the jetting frame.

The jetting nozzle may include a slit-shaped hole formed along a longitudinal direction of the jetting frame.

The filter part may include at least one of a pre filter, a hepa filter, an activated carbon filter, and a photo-catalyst filter.

When an angle formed between a flow of air jetted from the jetting nozzle and laundry arranged in the vertical direction is $\alpha$, and an angle formed between a flow of air suctioned into the filter part and the laundry arranged in the vertical direction is $\beta$, $\alpha$ and $\beta$ may be formed at acute angles.

The laundry care device may further include an air circulation device connected to the jetting unit and the suction unit and configured to generate a suction force for the suction unit to suction air and generate a jetting force for the jetting unit to jet air.

The air circulation device may include a circulation path provided between a suction path formed in the suction unit and a jetting path formed in the jetting unit and connecting the suction path to the jetting path.

The air circulation device may be disposed on at least one of one end in a longitudinal direction of the jetting unit and the suction unit and the other end opposite to the one end.

The laundry care device may further include a moving unit provided at one side of the laundry care device to move along a moving rail formed inside the cabinet.

The cabinet may include a stationary suction part formed therein such that contaminants flowing in an inner space of the cabinet are suctioned into the stationary suction part.

A laundry treating apparatus according to another aspect of the present disclosure includes: a cabinet; and a laundry care device disposed inside the cabinet to remove contaminants of laundry, wherein the laundry care device includes: a jetting unit configured to jet air toward the laundry; a suction unit into which air jetted from the jetting unit, after striking the laundry, is suctioned; and an air circulation device connected to the jetting unit and the suction unit, and configured to generate a suction force for the suction unit to suction air and generate a jetting force for the jetting unit to jet air.

The air circulation device may include a circulation path provided between a suction path formed in the suction unit and a jetting path formed in the jetting unit.

The laundry care device may be movably provided inside the cabinet.

The jetting unit, the suction unit, and the air circulation device may be integrally formed with each other.

A laundry care device according to an aspect of the present disclosure includes: a main body having a handle portion to be gripped; a jetting unit extending from the main body and jetting air toward laundry; and a suction unit integrally formed with the jetting unit and into which air jetted from the jetting unit, after passing through the laundry, is suctioned.

Advantageous Effects

According an aspect of the present disclosure, the efficiency of refreshing laundry can be enhanced by improving the structure of the laundry care device.

According an aspect of the present disclosure, the entire range of laundry can be subjected to laundry treatment by movably providing the laundry care device.

According an aspect of the present disclosure, the laundry care efficiency can be enhanced by keeping the inside of the laundry treating apparatus pleasant.

BEST MODES OF THE DISCLOSURE

Figure 1:
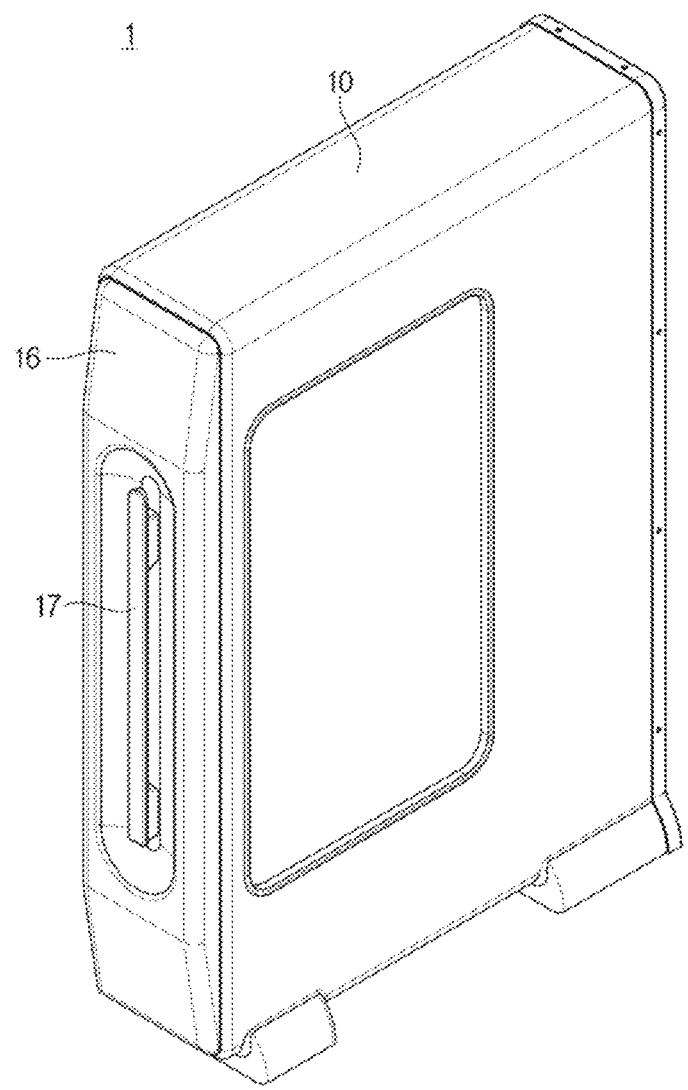
FIG. 1 is a perspective view illustrating a laundry treating apparatus according to an embodiment of the present disclosure.

While the present disclosure is susceptible to various modifications and alternative embodiments, specific embodiments thereof are shown by way of example in the drawings and will be described in detail. However, it should be understood that there is no intention to limit the present disclosure to the particular forms disclosed, rather the present disclosure is to cover all modifications, equivalents, and alternatives falling within the spirit and scope of the present disclosure.

Like numbers refer to like elements throughout the description of the drawings.

Meanwhile, terms used herein are used to aid in the explanation and understanding of the present disclosure and are not intended to limit the scope and spirit of the present disclosure. It should be understood that the singular forms "a," "an," and "the" also include the plural forms unless the context clearly dictates otherwise. The terms "comprises," "comprising," "includes," and/or "including," when used herein, specify the presence of stated features, integers, steps, operations, elements, components and/or groups thereof, and do not preclude the presence or addition of one or more other features, integers, steps, operations, elements, components, and/or groups thereof.

It will be understood that, although the terms first, second, A, B, etc. may be used herein to describe various elements, the elements should not be limited to the terms. The terms are only used to distinguish one element from another. For example, a first element could be termed a second element, and, similarly, a second element could be termed a first element, without departing from the scope of the present disclosure. As used herein, the term "and/or" includes any one or combinations of the associated listed items or any item of one or more of the associated listed items.

Hereinafter, embodiments according to the present disclosure will be described in detail with reference to the accompanying drawings.

Figure 2:
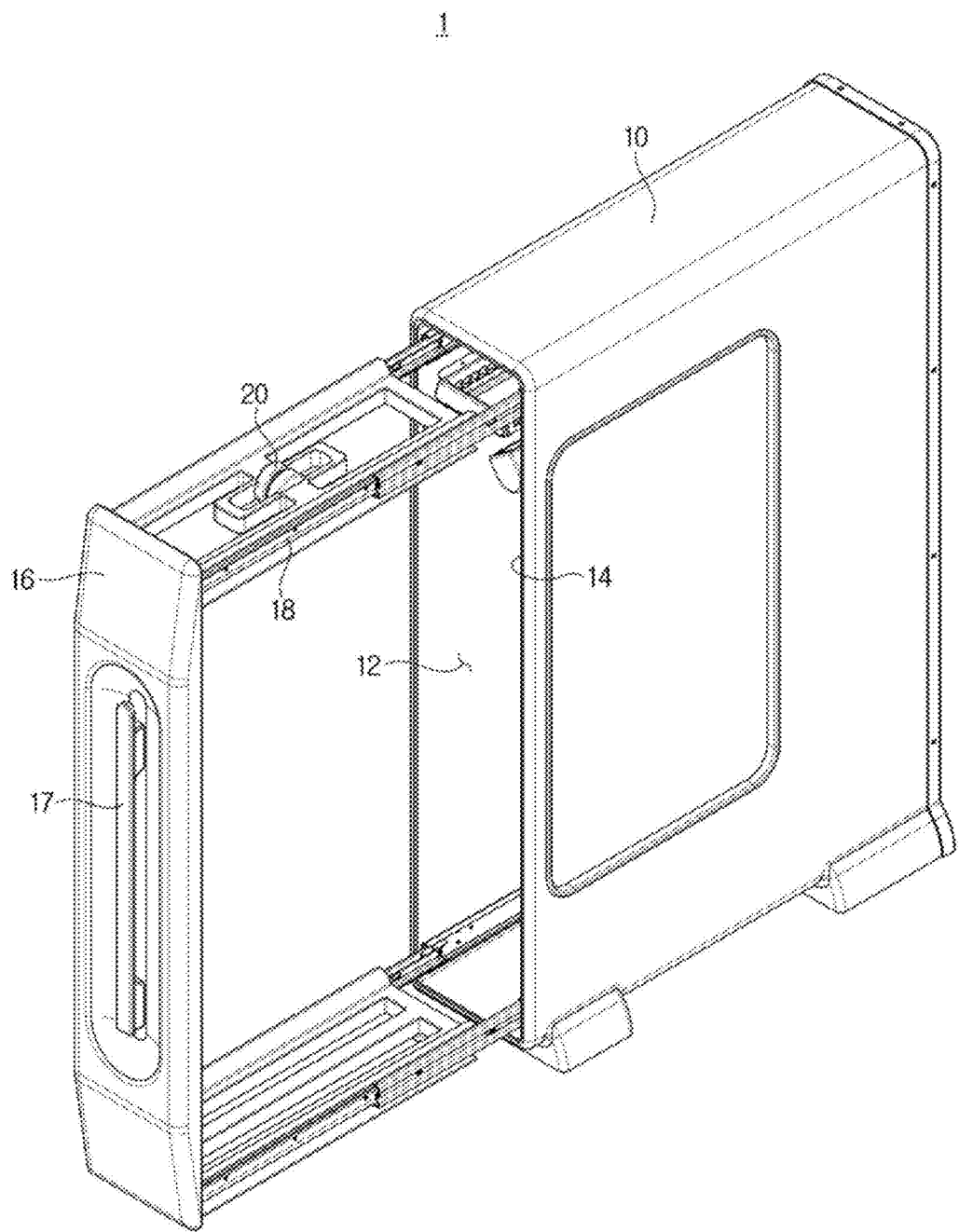
FIG. 2 is a perspective view illustrating the laundry treating apparatus according to the embodiment of the present disclosure.

FIG. 1 is a perspective view illustrating a laundry treating apparatus according to an embodiment of the present disclosure, and FIG. 2 is a perspective view illustrating the laundry treating apparatus according to the embodiment of the present disclosure.

A laundry treating apparatus 1 may include a cabinet 10 and a laundry care device 100.

The cabinet 10 is provided to hold laundry therein. An opening 14 may be formed at one side of the cabinet 10 for the entrance and exit of the laundry, and the opening 14 may be opened and closed by a door 16. The door 16 may be provided to slide with respect to the cabinet 10.

The door 16 may include a door arm 18 extending to the inside of the cabinet 10. The door arm 18 is provided with a sliding unit between the inner side surface of the cabinet 10 and the door arm 18 such that the door 16 is slidable with respect to the cabinet 10. The door arm 18 may include a laundry holder 20 for holding the laundry thereon. The door 16 is provided at one side thereof with a door handle 17 to be gripped to operate the door 16.

According to the present embodiment, the door 16 is slidably moved relative to the cabinet 10, but the present disclosure is not limited thereto. For example, the door 16 may be rotatably installed at one side of the cabinet 10 to open and close the opening 14. In this case, the laundry holder 20 may be provided to be located at an inside of the cabinet 10. The opening 14 and the door 16 may be implemented in various forms as long as it can allow laundry to be inserted into and withdrawn from the cabinet 10.

The laundry care device 100 may be provided to refresh laundry. In detail, the laundry care device 100 may be provided to remove contaminants in the laundry, remove dust adsorbed on the laundry, or smooth wrinkles generated in the laundry.

The laundry care device 100 may be disposed inside the cabinet 10, and may be movably provided in the cabinet 10. The configuration of the laundry care device 100 will be described below.

Figure 3:
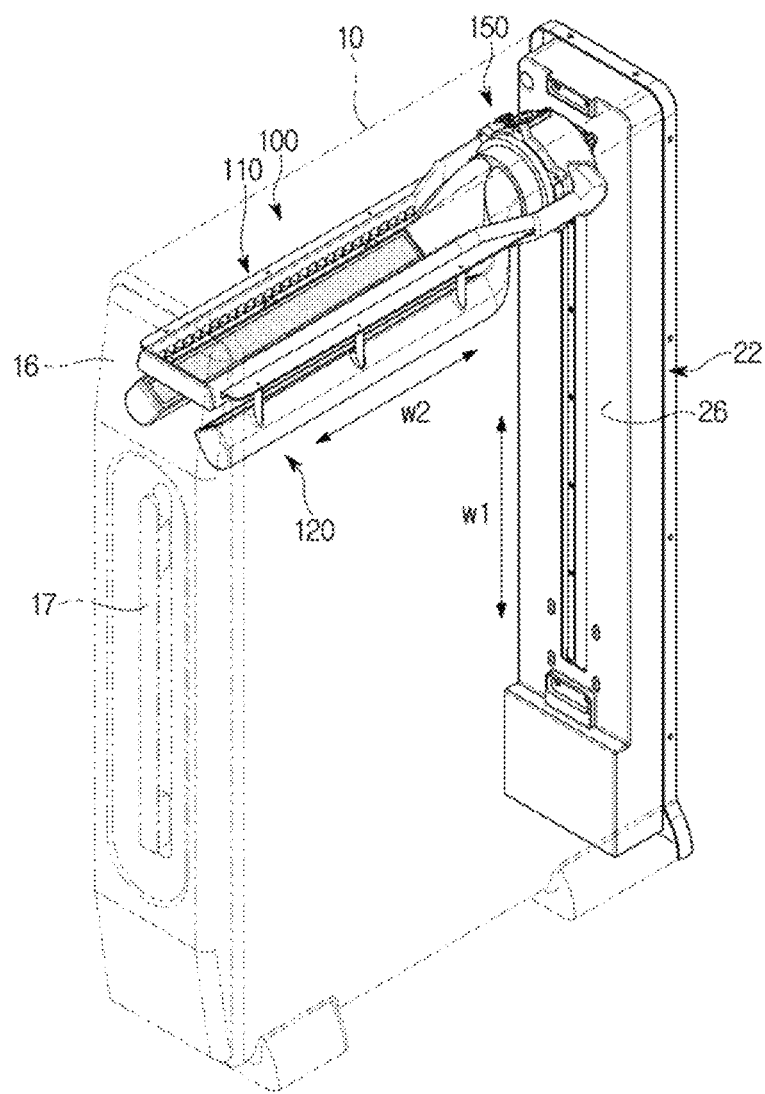
FIG. 3 is a view illustrating an inside of the laundry treating apparatus according to the embodiment of the present disclosure.
Figure 4:
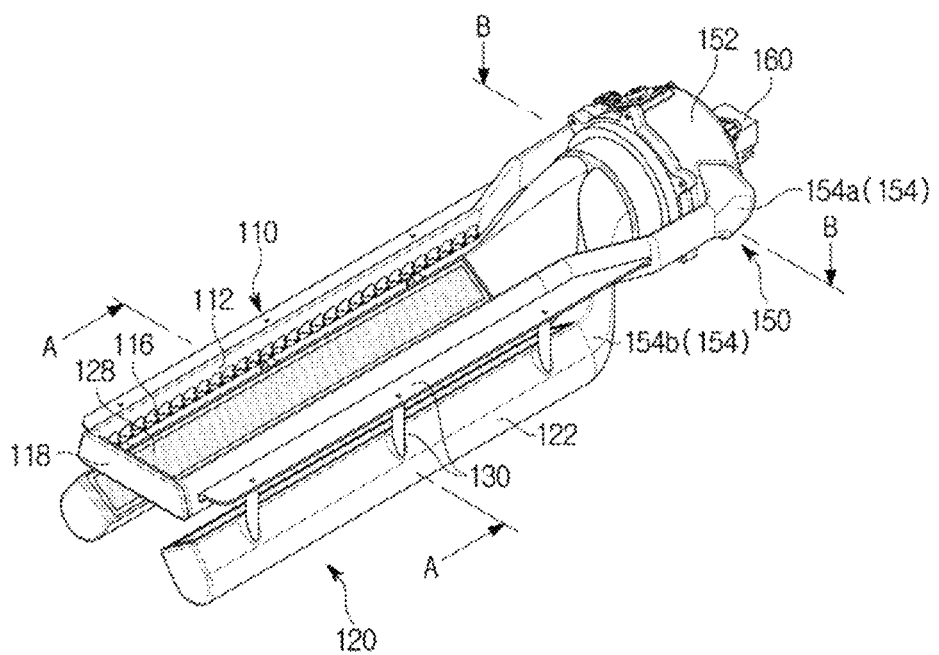
FIG. 4 is a perspective view illustrating a laundry care device according to the embodiment of the present disclosure.
Figure 5:
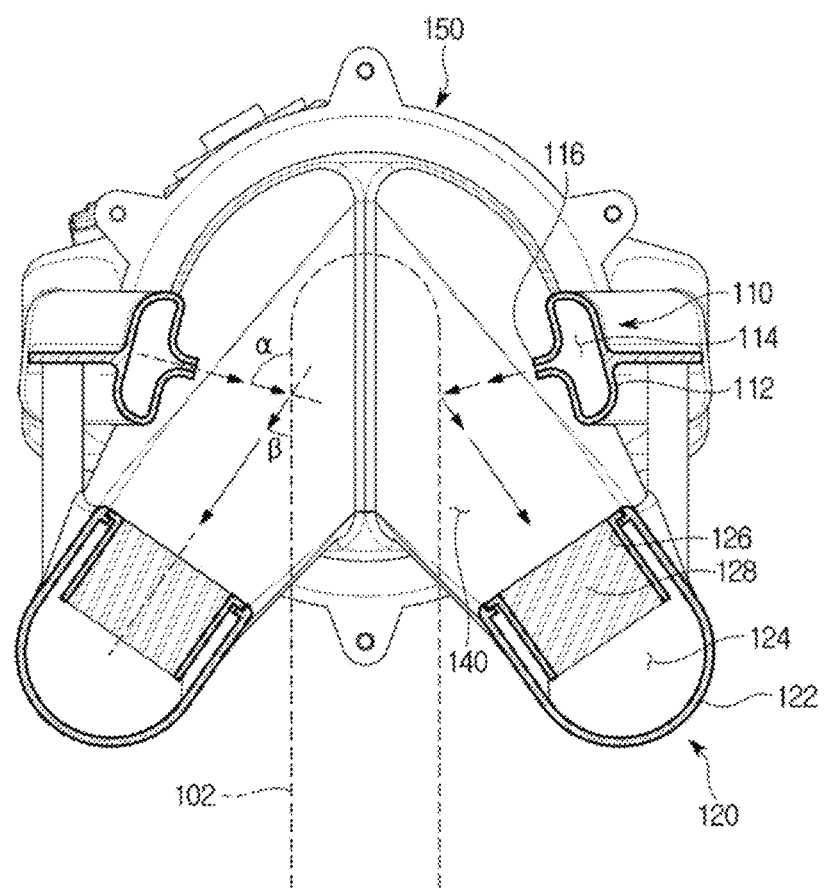
FIG. 5 is a sectional view taken along line A-A' of FIG. 4.
Figure 6:
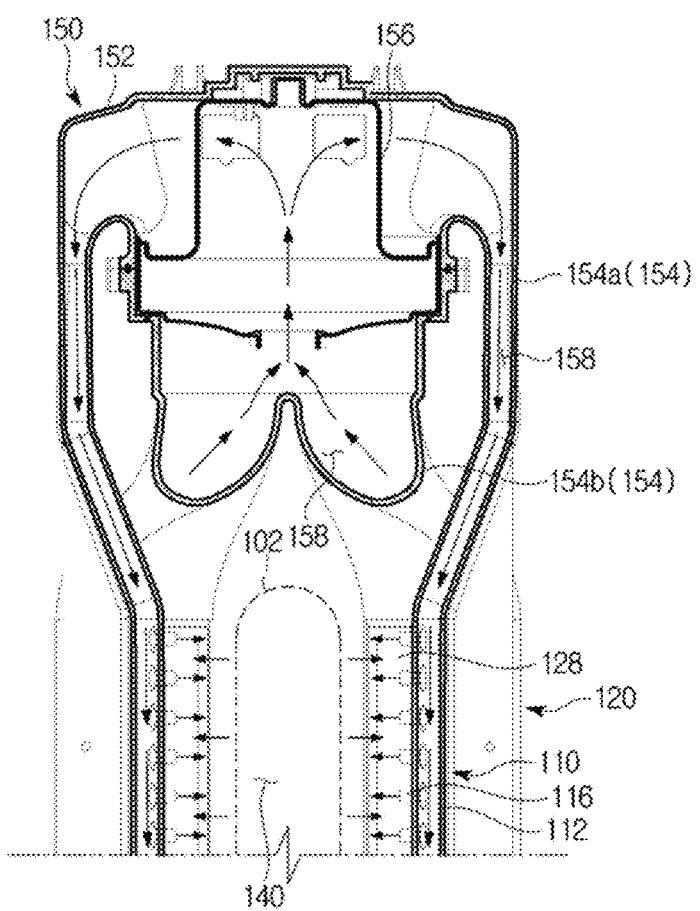
FIG. 6 is a sectional view taken along line B-B' of FIG. 4.

FIG. 3 is a view illustrating an inside of the laundry treating apparatus according to the embodiment of the present disclosure, FIG. 4 is a perspective view illustrating the laundry care device according to the embodiment of the present disclosure, FIG. 5 is a sectional view taken along line A-A' of FIG. 4, and FIG. 6 is a sectional view taken along line B-B' of FIG. 4.

The laundry care device 100 jets air, hot air, steam, or the like on laundry to improve the condition of the laundry. For the sake of convenience in description, it is assumed that air is jetted from the laundry care device 100. In addition, it should be understood that a heater or a steam generator may be added to the laundry care device 100 to jet not only air but also hot air or steam from the laundry care device 100.

The laundry care device 100 may include a jetting unit 110 and a suction unit 120.

The jetting unit 110 is provided to jet air toward laundry 102. The air jetted from the jetting unit 110 strikes the laundry to separate contaminants or dust adsorbed on the laundry, and smooth wrinkles of the laundry.

The suction unit 120 is provided to suction air. The suction unit 120 may be provided such that air jetted from the jetting unit 110 is suctioned into the suction unit 120 after passing through the laundry. In detail, the suction unit 120 may be disposed adjacent to the jetting unit 110 so that air jetted from the jetting unit 110 may be suctioned into the suction unit 120 after striking the laundry 102. The laundry care device 100 may be configured such that the flow of air jetted from the jetting unit 110 and the flow of air suctioned into the suction unit 120 form an angle of reflection with respect to the laundry. With this configuration, air jetted from the jetting unit 110, after striking the laundry and thus to be mixed with contaminants or dusts, is directly suctioned into the suction unit 120, so that the inside of the cabinet 10 may be prevented from being repeatedly contaminated.

The jetting unit 110 and the suction unit 120 may be provided in the same direction, that is, a longitudinal direction such that air jetted from the jetting unit 110 is suctioned into the suction unit 120 after passing through the laundry. In detail, when the laundry care device 100 is provided to be movable in a first direction W1, the jetting unit 110 and the suction unit 120 of the laundry care device 100 may be formed to have a longitudinal direction that is a second direction W2 perpendicular to the first direction W1.

The jetting unit 110 and the suction unit 120 may be each provided in a pair thereof such that the pair of jetting units 110 face each other and the pair of section units 120 face each other. A treatment space 140 may be formed between each pair of jetting units 110 and suction units 120 so that the laundry is positioned in the treatment space 140. The pair of jetting units 110 may be provided to face each other on both sides of the treatment space 140 with the treatment space 140 interposed therebetween, and the pair of suction units 120 may be provided on both sides of the treatment space 140 with the treatment space 140 interposed therebetween. With this configuration, one side of the laundry and the other side of the laundry opposite to the one side may be subjected to contamination treatment or wrinkle smoothing at the same time. However, the present disclosure is not limited thereto, and the laundry care device 100 may include a single jetting unit 110 and a single suction unit 120 such that the jetting unit 110 and the suction unit 120 are located only on one side of the laundry care device 100.

In addition, the present disclosure is not limited to the above, and the laundry care device 100 may include a plurality of jetting units 110 and a plurality of suction units 120 each corresponding to one of the plurality of jetting units 110. The laundry care device 100 may simultaneously perform laundry care on a plurality of pieces of laundry in a plurality of treatment spaces 140 formed between the jetting units 110 and the suction units 120.

The jetting unit 110 may include a jetting frame 112 and a jetting nozzle 116.

The jetting frame 112 may form a jetting path 114 in which jetted air flows.

The jetting nozzle 116 is provided to jet air toward the laundry. The jetting nozzle 116 is formed on the jetting frame 112 so that air flowing along the jetting path 114 may be jetted through the jetting nozzle 116. The jetting nozzle 116 is provided to have a jetting direction that is directed toward the laundry. The jetting direction of the jetting nozzle 116 may be configured to be directed to the laundry while being slanted downward. With this configuration, the air jetted from the jetting unit 110 may be efficiently suctioned into the suction unit 120 located at a lower side of the jetting unit 110 after passing through the laundry.

In other words, when an angle formed by the flow of air jetted from the jetting nozzle 116 and the laundry arranged in the vertical direction is $\alpha$, $\alpha$ may be provided to form an acute angle.

The jetting nozzle 116 may be provided at one side of the jetting frame 112 and may include a plurality of holes disposed to be spaced apart from each other. However, the form of the jetting nozzle 116 is not limited thereto. The shape of the jetting nozzle 116 is not limited thereto, and the use of the jetting nozzle 116 is satisfied as long as the jetting nozzle 116 can jet air toward the laundry, The suction unit 120 may include a suction frame 122 and a filter part 128.

The suction frame 122 may form a suction path 124 therein through which air suctioned into the suction frame 122 flows. The suction frame 122 and the jetting frame 112 may be disposed parallel to each other with a distance therebetween.

The filter part 128 may be provided to filter out contaminants from the air suctioned into the suction frame 122. The filter part 128 may be provided with one side open while facing the laundry. In more detail, the suction direction leading to the filter part 128 may be provided to be directed to the laundry while being slanted upward. With this configuration, the air jetted from the jetting unit 110 located at an upper side of the suction unit 120 may be efficiently suctioned into the suction unit 120 after passing through the laundry.

In other words, when an angle formed by the flow of air suctioned into the filter part 128 and the laundry arranged in the vertical direction is β, β may be formed at an acute angle.

The filter part 128 may be inserted into a frame opening 126 formed at one side in the longitudinal direction of the suction frame 122. The filter part 128 may be detachably provided on the suction frame 122 for replacement mounting. However, the filter part 128 according to the present disclosure is not limited thereto, and the filter part 128 may be formed integrally with the suction frame 122.

The type of the filter part 128 is not limited, and may be implemented using, for example, at least one of a pre-filter, a hepa filter, an activated carbon filter, and a photo-catalyst Filter.

Although the suction unit 120 has been illustrated as being located at a lower side of the jetting unit 110, the present disclosure is not limited thereto, and the suction unit 120 may be located at an upper side of the jetting unit 110. In this case, the jetting direction of the jetting nozzle 116 may be directed toward the laundry while being slanted upward, and the suction direction to the filter part 128 may be directed toward the laundry while being slanted downward.

The jetting unit 110 and the suction unit 120 may be integrally formed with each other. The laundry care device 100 is provided to be movable in the first direction W1 by a moving unit 160 which will be described below, and in this case, the jetting unit 110 and the suction unit 120 may move together by being integrally formed with each other. Further, the jetting unit 110 and the suction unit 120 may maintain an angle therebetween by being integrally formed with each other.

The laundry care device 100 may be provided with a support member 118 (see FIG. 4) between either pair of jetting units 110 or suction units 120 to connect the pair of jetting units 110 or suction units 120 to maintain a distance or angle between the pair of jetting units 110 or suction units 120. Referring to the drawing, the support member 118 is provided at one end of the pair of jetting units 110 to connect the pair of jetting units 110. However, the present disclosure is not limited thereto, and the support member 118 may connect the pair of suction units 120 to each other, or connect the pair of jetting units 110 to each other while connecting the pair of suction units 120 to each other.

The laundry care device 100 may include a connection mount member 130.

The connection mount member 130 is provided to connect the jetting unit 110 to the suction unit 120. The connection mount member 130 is provided to connect the jetting frame 112 of the jetting unit 110 to the suction frame 122 of the suction unit 120 while securing the jetting unit 110 and the suction unit 120 at a preset position and angle without being moved relative to each other. The laundry care device 100 may be formed as an integral structure by the connection mount member 130, but the present disclosure is not limited thereto, and the jetting unit 110 and the suction unit 120 may be formed as an integral structure by themselves.

The laundry care device 100 may include an air circulation device 150.

The air circulation device 150 allows air suctioned through the suction unit 120 to be jetted through the jetting unit 110 to circulate the air. That is, the air circulation device 150 generates a suction force for the suction unit 120 to suction air, and generates a jetting force for the jetting unit 110 to jet air. To this end, the air circulation device 150 is provided to be connected to the suction path 124 of the suction frame 122 and the jetting path 114 of the jetting frame 112. The air circulation device 150 may be integrally formed with the jetting unit 110 and the suction unit 120.

The air circulation device 150 may include a circulation path 158 connecting the suction path 124 to the jetting path 114, between the suction path 124 formed in the suction unit 120 and the jetting path 114 formed in the jetting unit 110. Air suctioned into the suction path 124 may be caused to flow into the jetting path 114 through the circulation path 158.

The air circulation device 150 may include a main body 152, a connection frame 154, and a fan motor 156.

The main body 152 is provided to have the fan motor 156 disposed therein. The fan motor 156 is provided to generate a suction force at the suction unit 120 and a jetting force at the jetting unit 110.

The connection frame 154 may be provided to connect the main body 152 to the suction unit 120 and the jetting unit 110. The air circulation device 150 may include the circulation frame 158 formed inside the connection frame 154 and the main body 152. The circulation path 158 may be provided to connect the suction path 124 to the jetting path 114. The connection frame 154 includes a first connection frame 154a connecting the main body 152 to the jetting unit 110 and a second connection frame 154b connecting the main body 152 to the suction unit 120.

The air circulation device 150 may be disposed at least one of one end and the other end in the longitudinal direction of the jetting unit 110 and the suction unit 120. However, the arrangement of the air circulation device 150 is not limited thereto, and the use of the configuration of the air circulation device 150 is satisfied as long as the air circulation device 150 is connected to the jetting unit 110 and the suction unit 120 to generate a jetting force and a suction force, respectively.

Figure 7:
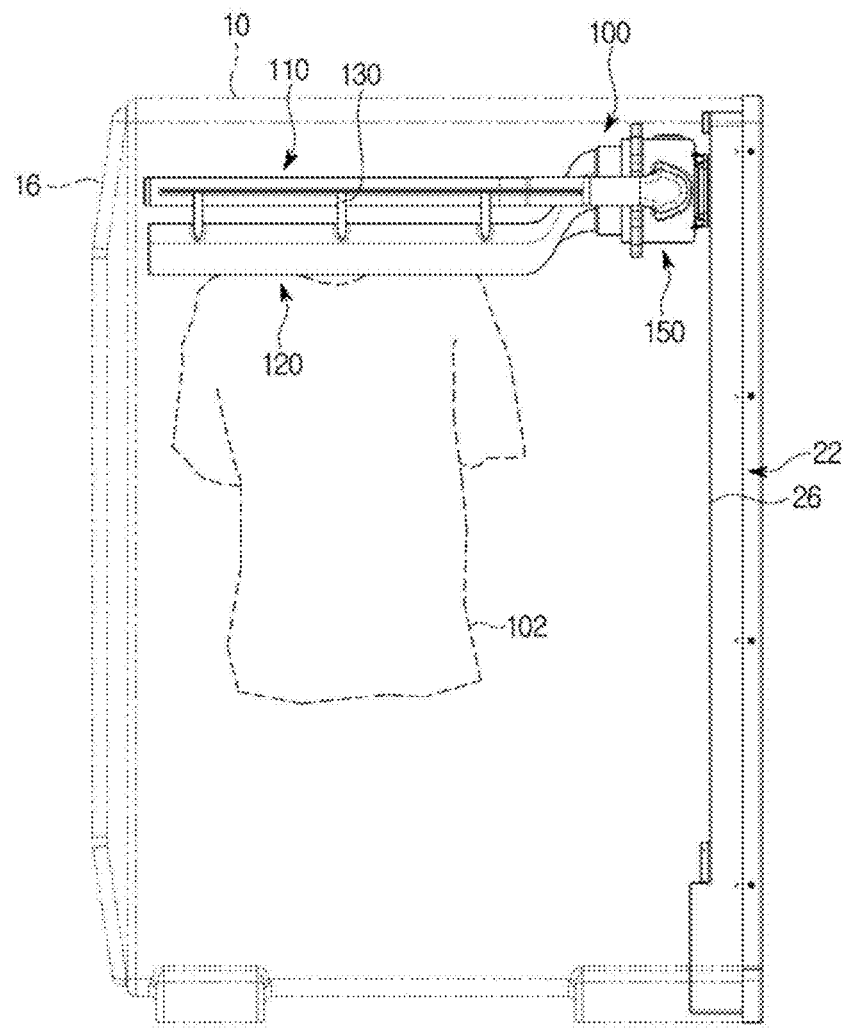
FIG. 7 is a front view illustrating the inside of the laundry treating apparatus according to the embodiment of the present disclosure.
Figure 8:
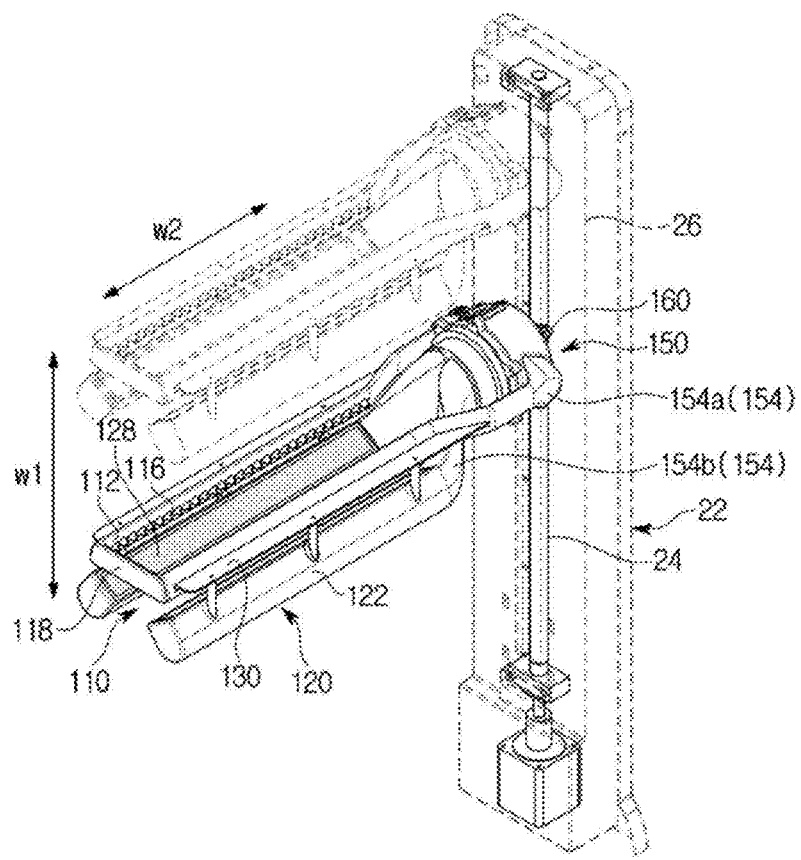
FIG. 8 is a view illustrating an operation of the laundry treating apparatus according to the embodiment of the present disclosure.

FIG. 7 is a front view illustrating the inside of the laundry treating apparatus according to the embodiment of the present disclosure, and FIG. 8 is a view illustrating an operation of the laundry treating apparatus according to the embodiment of the present disclosure.

The laundry care device 100 is movably provided. According to the embodiment, the laundry care device 100 is configured to reciprocate in the up and down direction, but the movement direction of the laundry care device 100 is not limited thereto.

Referring to FIG. 6, the length of the laundry care device 100 may be provided to correspond to the width of laundry. In detail, each of the lengths of the jetting unit 110 and the suction unit 120 may be provided to correspond to the width of laundry. With this configuration, the laundry care device 100 allow the jetting unit 110 and the suction unit 120 formed in the longitudinal direction that is the second direction W2 to reciprocate in the first direction W1 as if scanning the laundry so that the entire range of the laundry is subjected to the operation of the jetting unit 110 and the suction unit 120.

The laundry care device 100 may include the moving unit 160.

The moving unit 160 may be provided to be moved in the first direction by a moving device 22. The moving device 22 may include a rail bracket 26 forming the external appearance thereof and a moving rail 24 formed in the rail bracket 26 and having a length direction in the first direction.

The moving unit 160 is configured to be movable along the moving rail 24 formed inside the cabinet 10. The moving unit 160 may be integrally formed with the laundry care device 100. The configuration of the moving unit 160 and the moving rail 24 is not limited thereto and may be variously configured as long as it can allow the laundry care device 100 to be movable.

Hereinafter, the operation of the laundry treating apparatus described above will be described.

The door 16 of the cabinet 10 is opened to hold laundry in the cabinet 10, and then the door 16 is closed.

Then, the laundry care device 100 reciprocates in the up and down direction.

In the process of the laundry care device 100 being moved, air is jetted from the jetting nozzle 116 of the jetting unit 110 by the air circulation device 150 to strike the laundry, which causes contaminants or dust adsorbed to the laundry to be removed or wrinkles to be smoothed. Air jetted from the jetting unit 110 and striking the laundry is suctioned into the suction unit 120. As the air jetted from the jetting unit 110 and striking the laundry is directly suctioned into the suction unit 120, the contaminated air is prevented from repeatedly contaminating the inside of the cabinet 10.

When the air is suctioned into the suction unit 120, contaminant or dust is filtered out by the filter part 128, and the purified air is again jetted through the jetting unit 110 by the air circulation unit 150, to strike the laundry.

By repeating the above described process, the entire range of the laundry is refreshed.

Hereinafter, a laundry treating apparatus according to another embodiment of the present disclosure will be described.

In the following description, configurations identical to those described in the previous embodiment will be omitted.

Figure 9:
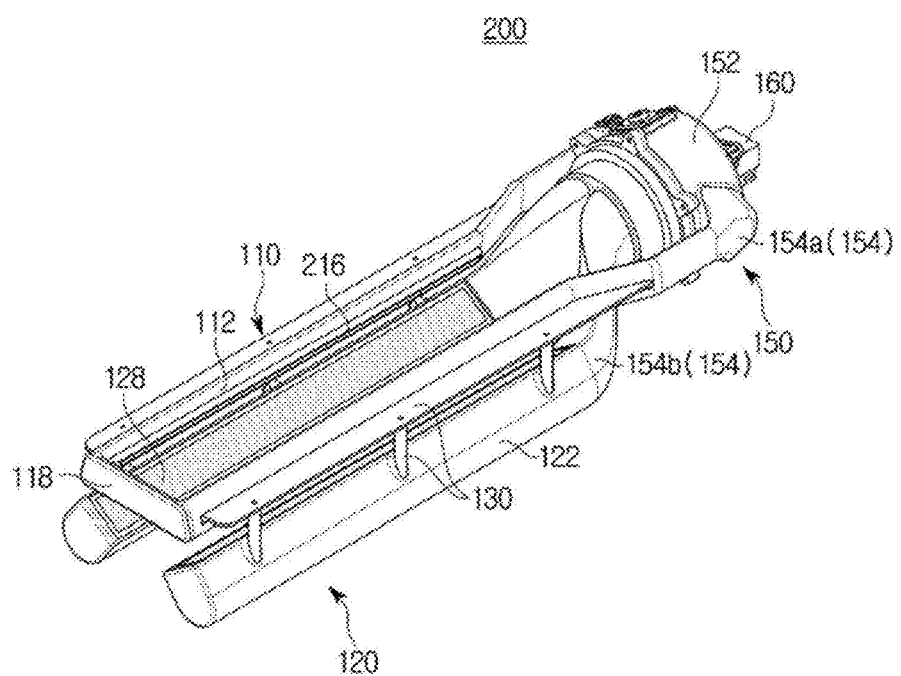
FIG. 9 is a perspective view illustrating a laundry care device according to another embodiment of the present disclosure.

FIG. 9 is a perspective view illustrating a laundry care device according to another embodiment of the present disclosure.

A jetting unit 210 may include a jetting frame 112 and a jetting nozzle 216.

The jetting nozzle 216 is provided to jet air toward laundry. The jetting nozzle 216 is provided to have a jetting direction that is directed to the laundry. The jetting nozzle 216 may be configured to be directed to the laundry while being slanted downward. With this configuration, the air jetted from the jetting unit 210 and passing through the laundry may be efficiently suctioned into the suction unit 120 located at a lower side of the jetting unit 210.

The jetting nozzle 216 may include a slit-shaped hole formed along the longitudinal direction of the jetting frame 112. A plurality of the slit-shaped holes may be arranged in parallel to each other, and may be disposed to be spaced apart from each other while being arranged in the longitudinal direction.

The shape of the jetting nozzle 216 is not limited thereto, and the use of the jetting nozzle 216 is satisfied as long as the jetting nozzle can jet air toward laundry.

Hereinafter, a laundry treating apparatus according to another embodiment of the present disclosure will be described.

In the following description, configurations identical to those described in the previous embodiment will be omitted.

Figure 10:
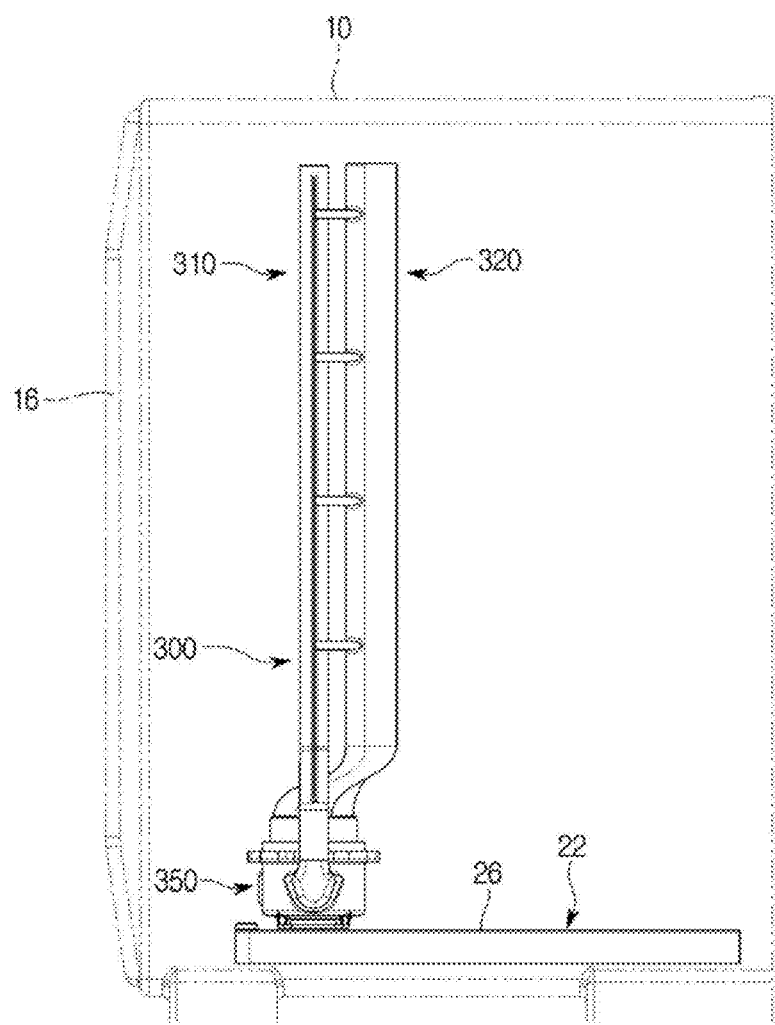
FIG. 10 is a front view illustrating an inside of a laundry treating apparatus according to another embodiment of the present disclosure.
Figure 11:
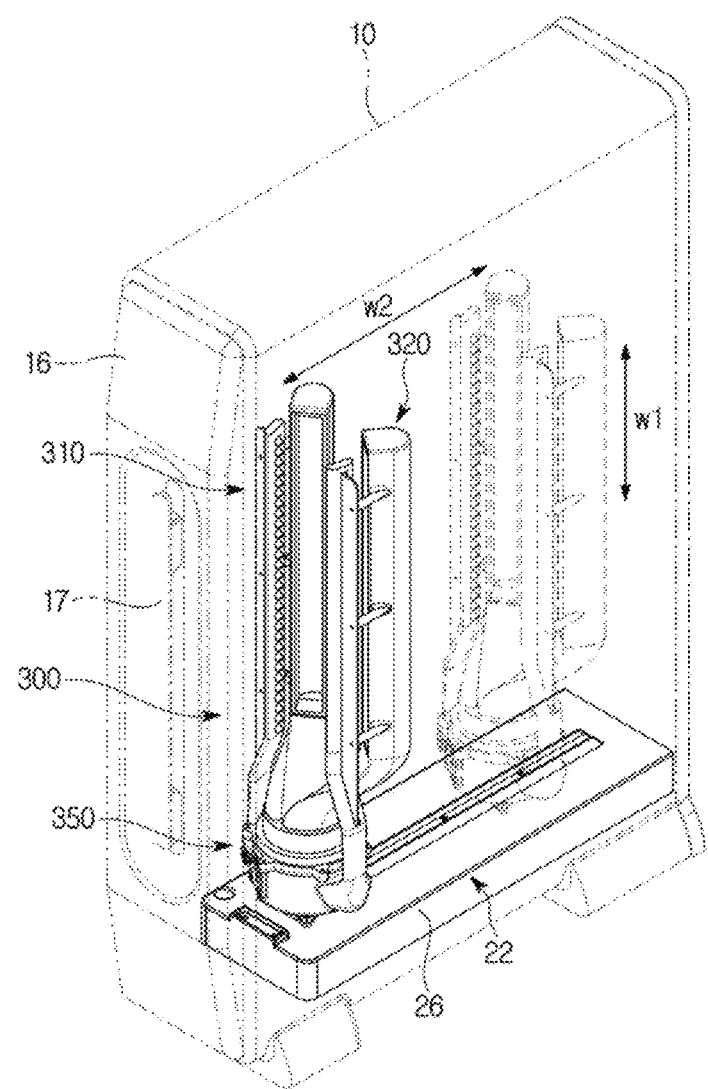
FIG. 11 is a view illustrating an operation of a laundry care device provided in a laundry treating apparatus according to another embodiment of the present disclosure.

FIG. 10 is a front view illustrating the inside of a laundry treating apparatus according to another embodiment of the present disclosure, and FIG. 11 is a view illustrating an operation of a laundry care device provided in the laundry treating apparatus according to the embodiment of the present disclosure.

A laundry care device 300 may be provided to be movable in the left and right direction.

The length of the laundry care device 300 may correspond to the vertical length of laundry. In detail, the lengths of a jetting unit 310 and a suction unit 320 may correspond to the vertical length of laundry. An air circulation device 350 may be provided at an end of the jetting unit 310 and the suction unit 320. With this configuration, the laundry care device 100 provided with the jetting unit 310 and the suction unit 320 formed in the longitudinal direction that is the first direction W1 may reciprocate in the second direction W2 as if scanning the laundry such that the entire range of the laundry is subjected to operation of the jetting unit 310 and the suction unit 320.

The laundry care device 300 may include a moving unit 360.

The moving unit 360 may be provided to be movable in the second direction by a moving device 22. The moving device 22 may include a rail bracket 26 forming the external appearance and a moving rail 24 formed in the rail bracket 26 in a longitudinal direction that is the second direction.

The moving unit 360 is configured to be movable along the moving rail 24 formed inside the cabinet 10. The moving unit 360 may be integrally formed with the laundry care device 100. The configuration of the moving unit 360 and the moving rail 24 is not limited thereto as long as it can allow the laundry care device 300 to be movable.

Hereinafter, a laundry processing device 1 according to another embodiment of the present disclosure will be described.

In the following description, configurations identical to those described in the previous embodiment will be omitted.

Figure 12:
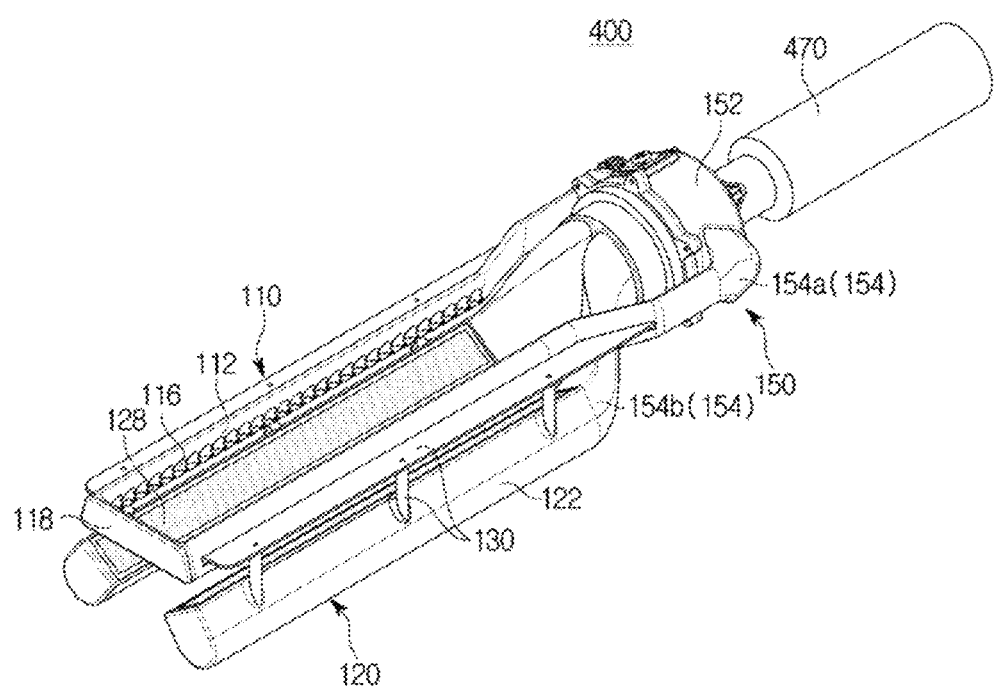
FIG. 12 is a perspective view illustrating a laundry care device according to another embodiment of the present disclosure.

FIG. 12 is a perspective view illustrating a laundry care device according to another embodiment of the present disclosure.

A laundry care device 400 may be movably provided.

The laundry care device 400 may include a handle portion 470 for gripping. The handle portion 470 allows a jetting unit 110 and a suction unit 120 of the laundry care device 400 to be placed adjacent to laundry or laundry to be placed in a treatment space 140 to remove contaminants or dust of the laundry, or smooth wrinkle of the laundry.

Power supply to an air circulation device 150 of the laundry care device 400 may be achieved with a separate rechargeable power source (not shown) or by connecting electric wires.

Hereinafter, a laundry treating apparatus according to another embodiment of the present disclosure will be described.

In the following description, configurations identical to those described in the previous embodiment will be omitted.

Figure 13:
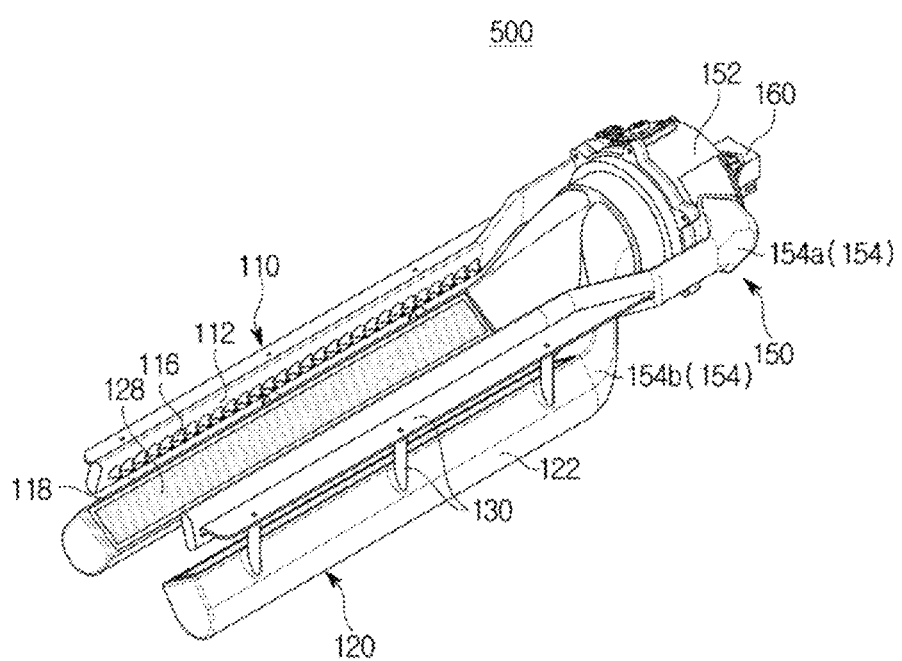
FIG. 13 is a perspective view illustrating a laundry care device according to another embodiment of the present disclosure.
Figure 14:
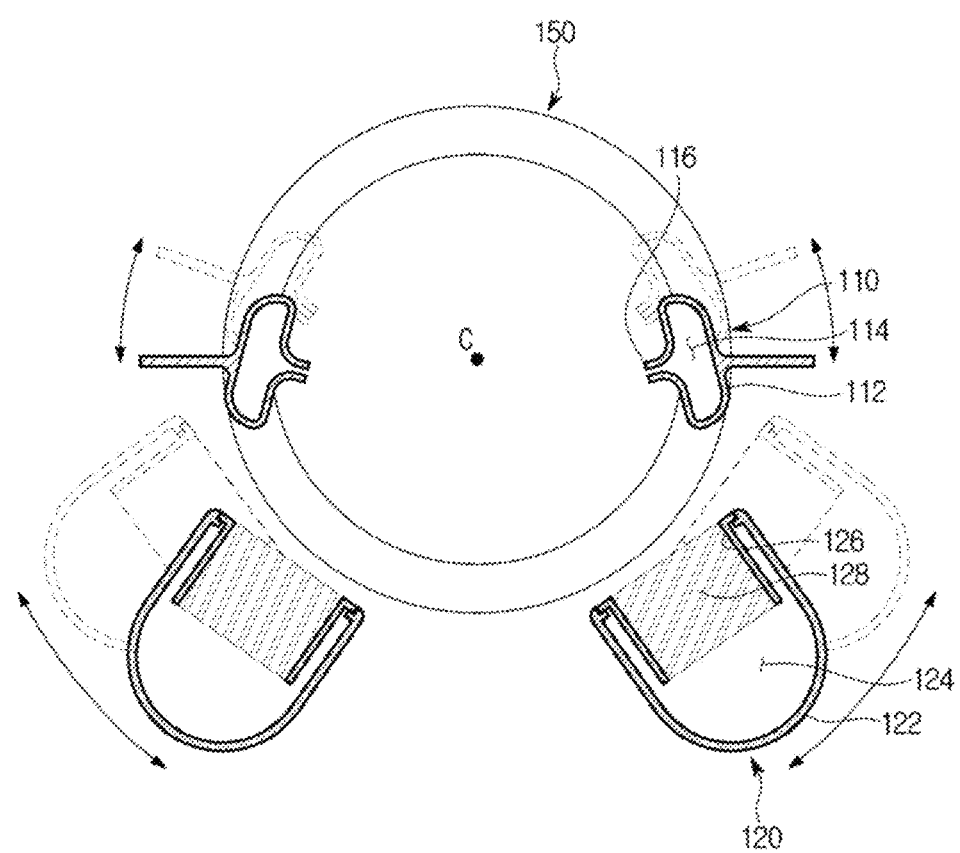
FIG. 14 is a view illustrating an operation of the laundry care device according to the embodiment of the present disclosure.

FIG. 13 is a perspective view illustrating a laundry care device according to another embodiment of the present disclosure, and FIG. 14 is a view illustrating an operation of the laundry care device according to the embodiment of the present disclosure.

A laundry care device 500 may include a jetting unit 510 and a suction unit 520.

The jetting unit 510 is provided to jet air toward laundry.

The jetting unit 510 may include a jetting frame 112 and a jetting nozzle 116. The jetting frame 112 may form a jetting path 114 in which jetting air flows.

The suction unit 520 may include a suction frame 122 and a filter part 128.

The suction frame 122 may form a suction path 124 in which air suctioned into the suction frame 122 flows.

The jetting unit 510 and the suction unit 520 may be provided to be rotatable with respect to an air circulation device 150. For the sake of convenience in description, the jetting unit 510 includes a first jetting unit 510a and a second jetting unit 510b, and the suction unit 520 includes a first suction unit 520a and a second suction unit 520b corresponding to the first jetting unit 510a and the second jetting unit 510b, respectively.

The first jetting unit 510a and the first suction unit 520a form a first module and may be rotatable about a rotation axis C passing through the air circulation unit 150. The second jetting unit 510b and the second suction unit 520b also form a second module and may be rotatable about the rotation axis C passing through the air circulation device 150.

The first module and the second module may rotate about the rotation axis C independent of each other, or may rotate symmetrical to each other. With this operation, the distance between the first and second modules and the laundry and the angle formed between the first and second modules and the laundry may be adjusted according to the thickness, type, and the like of the laundry in a treatment space 140 formed between the first module and the second module. Although the first and second modules according the present embodiment are illustrated as rotating about the rotation axis, the present disclosure is not limited thereto. For example, the laundry care device 500 may include a component configured to widen or narrow the distance between the first module and the second module by moving back and forth.

In addition, according to the present embodiment, the first jetting unit 510a and the first suction unit 520a forming the first module move together while being secured to each other, and the second jetting unit 510b and the second suction unit 520b forming the second module move together while being secured to each other. However, the present disclosure is not limited thereto. For example, the first jetting unit 510a and the first suction unit 520a may each have a separate moving structure, and move independently of each other. In addition, the second jetting unit 510b and the second suction unit 520b may each have a separate moving structure, and move independently of each other. That is, the laundry care device 500 may have a structure in which a distance, an angle, and the like between the jetting units 510 and those between the suction units 520 are varied depending on the thickness and type of the laundry.

Hereinafter, a laundry treating apparatus according to another embodiment of the present disclosure will be described.

In the following description, configurations identical to those described in the previous embodiment will be omitted.

Figure 15:
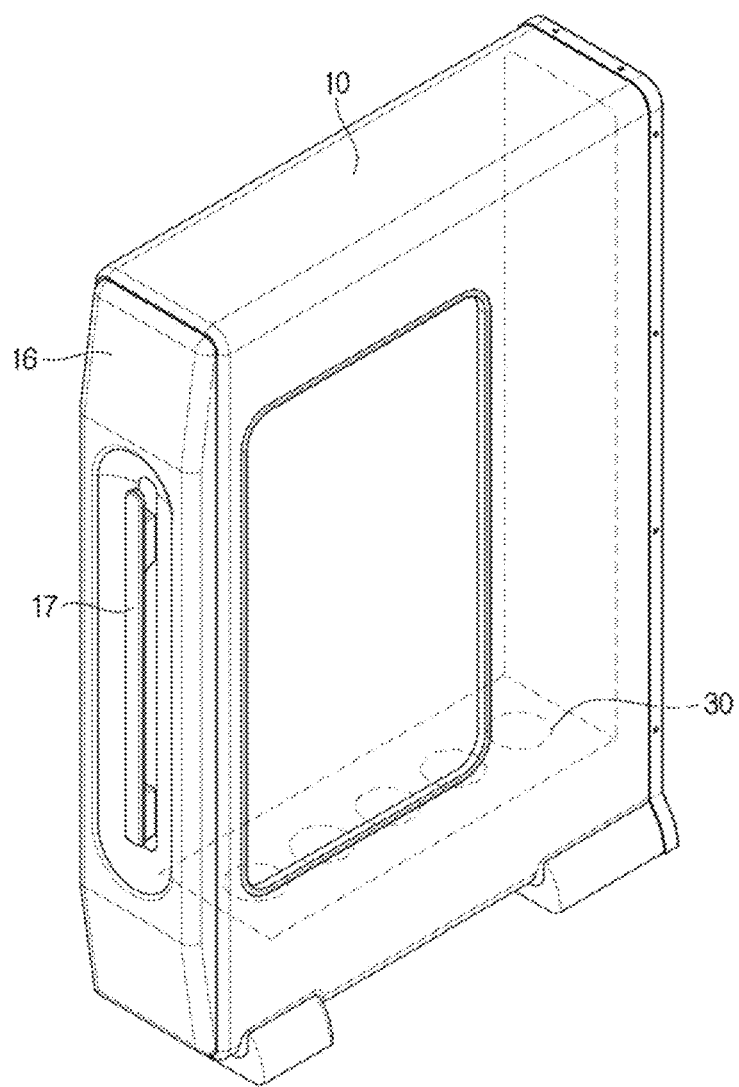
FIG. 15 is a perspective view illustrating a laundry treating apparatus according to another embodiment of the present disclosure.

FIG. 15 is a perspective view illustrating a laundry treating apparatus according to another embodiment of the present disclosure.

A laundry treating apparatus 1 may include a cabinet 10 and a laundry care device 100.

The cabinet 10 is provided to hold laundry therein. An opening 14 may be formed at one side of the cabinet 10 for the entrance and exit of laundry, and the opening 14 may be opened and closed by a door 16. The door 16 may be provided to slide relative to the cabinet 10.

The laundry care device 100 is provided to refresh laundry. In detail, the laundry care device 100 may be provided to remove contaminants in laundry, remove dust adsorbed on laundry, or smooth wrinkles generated in laundry.

The cabinet 10 may include a stationary suction part 30 for suctioning contaminants, dust, and the like flowing in an inner space 12 therein. Contaminants, dust, or the like flowing in the cabinet 10 may be suctioned into the suction unit 120 of the laundry care device 100, and contaminants and dust that are not suctioned into the suction unit 120 may be filtered out and discharged through the stationary suction part 30 of the cabinet 10 so that the inner space 12 of the cabinet 10 is kept from being contaminated.

Hereinafter, a laundry treating apparatus according to another embodiment of the present disclosure will be described.

In the following description, configurations identical to those described in the previous embodiment will be omitted.

Figure 16:
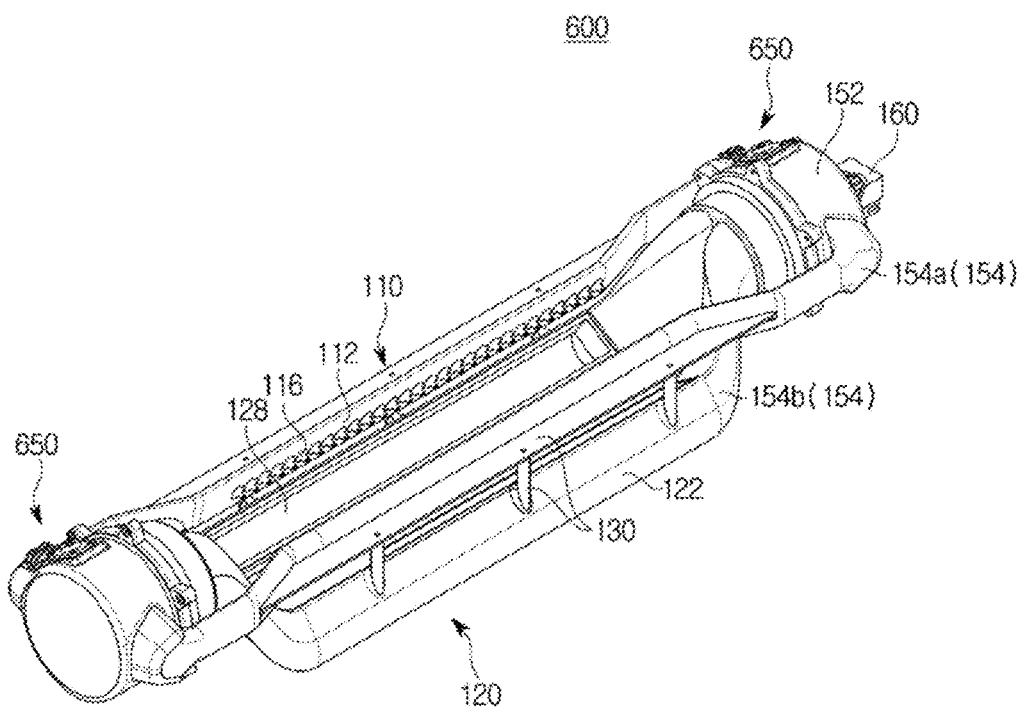
FIG. 16 is a perspective view illustrating a laundry care device according to another embodiment of the present disclosure.
Figure 17:
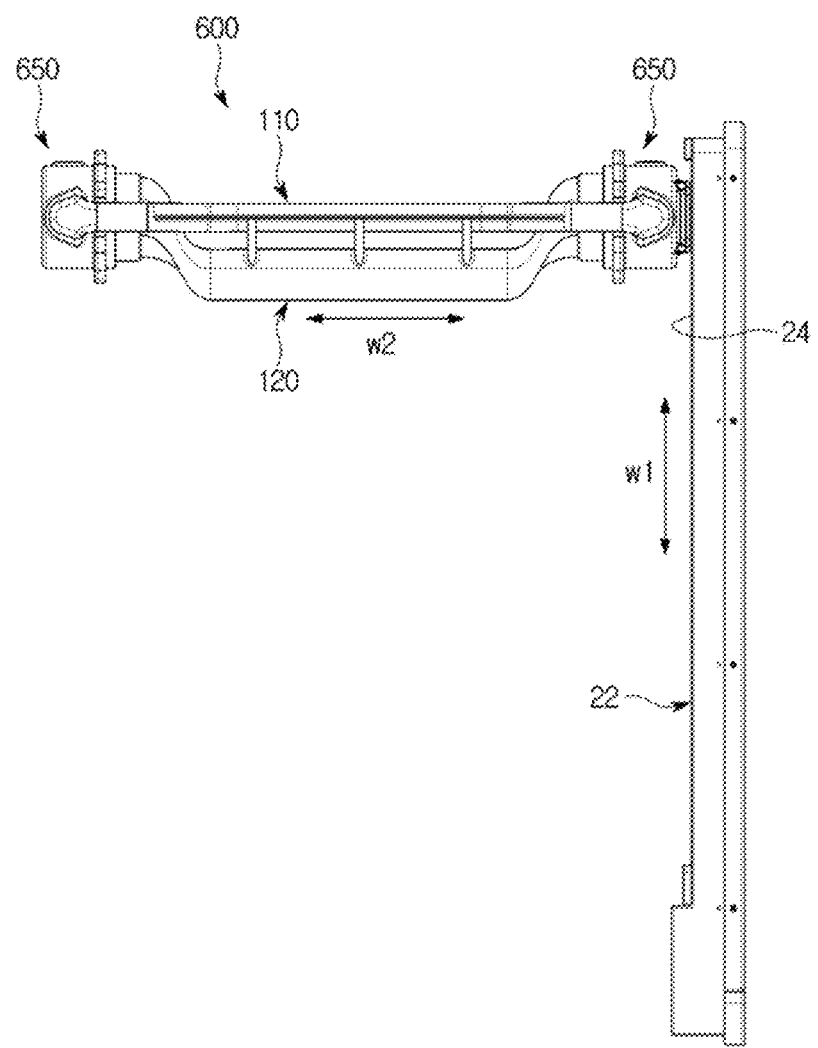
FIG. 17 is a view illustrating an operation of a laundry treating apparatus according to another embodiment of the present disclosure.

FIG. 16 is a perspective view illustrating a laundry care device according to the embodiment of the present disclosure, and FIG. 17 is a view illustrating an operation of the laundry treating apparatus according to the embodiment of the present disclosure.

A laundry care device 600 may include an air circulation device 650.

The air circulation device 650 allows air suctioned through a suction unit 120 to be jetted through a jetting unit 110 so that air is circulated. That is, the air circulation device 650 generates a suction force for the suction unit 120 to suction air, and generates a jetting force for the jetting unit 110 to jet air.

The air circulation devices 650 may be provided at opposite ends of the jetting unit 110 and the suction unit 120. That is, the laundry care device 600 may include a pair of air circulation devices 650, and may be configured to operate at least one of the pair of air circulation devices 650. With this configuration, a jetting force and a suction force may be provided to the entire area of the jetting unit 110 and the suction unit 120.

Although few embodiments of the present disclosure have been shown and described, the above embodiment is illustrative purpose only, and it would be appreciated by those skilled in the art that changes and modifications, which have not been illustrated above, may be made in these embodiments without departing from the principles and scope of the disclosure, the scope of which is defined in the claims and their equivalents.

The invention claimed is:

1. A laundry treating apparatus comprising
a cabinet; and
a laundry care device movably provided inside the cabinet,
wherein the laundry care device includes:
a jetting unit configured to jet air in a first direction toward the laundry; and
a suction unit configured to suction air jetted by the jetting unit after the jetted air strikes the laundry, the suctioning of the air being in a second direction which is at an angle with respect to the first direction, the jetting unit and the suction unit both being configured to face a same side of the laundry,
wherein the cabinet includes a stationary suction part formed therein such that contaminants flowing in an inner space of the cabinet are suctioned into the stationary suction part,
wherein the suction unit is located at a lower side of the jetting unit,
wherein the jetting unit includes a jetting nozzle configured to jet air toward the laundry while being slanted downward, and
wherein the suction unit includes a filter part directed to the laundry while being slanted upward such that air jetted from the jetting nozzle, after striking the laundry, is suctioned.

2. The laundry treating apparatus of claim 1, wherein the laundry care device is provided to be movable in a third direction, and the jetting unit and the suction unit each are provided with a longitudinal direction that is a fourth direction perpendicular to the third direction and are disposed in parallel with each other.

3. The laundry treating apparatus of claim 1, wherein the jetting unit and the suction unit are integrally formed with each other.

4. The laundry treating apparatus of claim 1, wherein
the jetting unit includes:
  a first jetting unit and a second jetting unit disposed symmetrical to each other, and
the suction unit includes:
  a first suction unit into which air jetted from the first jetting unit, after striking the laundry, is suctioned; and
  a second suction unit disposed symmetrical to the first suction unit and into which air jetted from the second jetting unit, after striking the laundry, is suctioned,
wherein the first jetting unit and the first suction unit are movable relative to the first jetting unit and the second suction unit,
wherein the first jetting unit and the first suction unit are configured to be on a first side of the laundry and the second jetting unit and the second suction unit are configured to be on a second side of the laundry.

5. The laundry treating apparatus of claim 1, wherein the suction unit further includes a suction frame provided at an inside thereof with a suction path that allows air suctioned through the filter part to pass therethrough, and on which the filter part is disposed, and
  wherein the jetting unit further includes:
  a jetting frame provided at an inside thereof with a jetting path that allows air suctioned into the suction path to pass therethrough, and on which the jetting nozzle is disposed.

6. The laundry treating apparatus of claim 5, wherein the jetting nozzle includes a plurality of jetting holes disposed to be spaced apart from each other along a longitudinal direction of the jetting frame.

7. The laundry treating apparatus of claim 5, wherein the jetting nozzle includes a slit-shaped hole formed along a longitudinal direction of the jetting frame.

8. The laundry treating apparatus of claim 1, wherein the filter part includes at least one of a pre filter, a hepa filter, an activated carbon filter, and a photo-catalyst filter.

9. The laundry treating apparatus of claim 1, wherein when an angle formed between a flow of air jetted from the jetting nozzle and laundry arranged in the vertical direction is a, and an angle formed between a flow of air suctioned into the filter part and the laundry arranged in the vertical direction is $\beta$, $\alpha$ and $\beta$ are formed at acute angles.

10. The laundry treating apparatus of claim 1, wherein the laundry care device further includes an air circulation device connected to the jetting unit and the suction unit and configured to generate a suction force for the suction unit to suction air and generate a jetting force for the jetting unit to jet air.

11. The laundry treating apparatus of claim 10, wherein the air circulation device includes a circulation path provided between a suction path formed in the suction unit and a jetting path formed in the jetting unit and connecting the suction path to the jetting path.

12. The laundry treating apparatus of claim 10, wherein the air circulation device is disposed on at least one of one end in a longitudinal direction of the jetting unit and the suction unit and the other end opposite to the one end.

13. The laundry treating apparatus of claim 1, wherein the laundry care device further includes a moving unit provided at one side of the laundry care device to move along a moving rail formed inside the cabinet.

* * * * *

UNITED STATES PATENT AND TRADEMARK OFFICE
CERTIFICATE OF CORRECTION

PATENT NO. : 11,168,426 B2
APPLICATION NO. : 16/324363
DATED : November 9, 2021
INVENTOR(S) : Hwang Mook Cho et al.

Page 1 of 1

It is certified that error appears in the above-identified patent and that said Letters Patent is hereby corrected as shown below:

In the Claims

Column 14, Line 13:
Claim 9, delete "is a," and insert -- is $\alpha$, --, therefor.

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*